(12) United States Patent
Melkent (10) Patent No.: US 10,828,113 B2
(45) Date of Patent: Nov. 10, 2020

(54) SYSTEM AND METHOD FOR PERFORMING AND EVALUATING A PROCEDURE

(71) Applicant: Medtronic Navigation, Inc., Louisville, CO (US)

(72) Inventor: Anthony J. Melkent, Germantown, TN (US)

(73) Assignee: Medtronic Navigation, Inc., Louisville, CO (US)

( * ) Notice: Subject to any disclaimer, the term of this patent is extended or adjusted under 35 U.S.C. 154(b) by 199 days.

(21) Appl. No.: 15/997,246

(22) Filed: Jun. 4, 2018

(65) Prior Publication Data

US 2019/0365476 A1 Dec. 5, 2019

(51) Int. Cl.
*A61B 34/20* (2016.01)
*A61B 34/10* (2016.01)
*A61F 2/44* (2006.01)

(52) U.S. Cl.
CPC .............. *A61B 34/20* (2016.02); *A61B 34/10* (2016.02); *A61B 2034/2051* (2016.02); *A61B 2034/2055* (2016.02); *A61B 2034/2063* (2016.02); *A61F 2/442* (2013.01); *A61F 2/4455* (2013.01)

(58) Field of Classification Search
CPC . A61B 34/20; A61B 34/10; A61B 2034/2051; A61B 2034/2055; A61B 2034/2063
See application file for complete search history.

(56) References Cited

U.S. PATENT DOCUMENTS

| | | | |
|---|---|---|---|
| 7,542,791 B2 | 6/2009 | Mire et al. | |
| 7,697,972 B2 | 4/2010 | Verard et al. | |
| RE44,305 E | 6/2013 | Foley et al. | |
| 8,644,907 B2 | 2/2014 | Hartmann et al. | |
| 8,842,893 B2 | 9/2014 | Teichman et al. | |
| 2003/0028091 A1* | 2/2003 | Simon | A61B 6/12 600/407 |
| 2004/0199072 A1 | 10/2004 | Sprouse et al. | |
| 2017/0265774 A1* | 9/2017 | Johnson | A61B 34/30 |

FOREIGN PATENT DOCUMENTS

EP 3165192 A2 5/2017

OTHER PUBLICATIONS

International Search Report dated Sep. 10, 2019 in corresponding PCT application PCT/US2019/035204.
Written Opinion dated Sep. 10, 2019 in corresponding PCT application PCT/US2019/035204.
Jochen Wurm et al. Intra-operative image update: first experiences with new softward in computer-assisted sinus surgery, International Journal of Medical Robotics and Computer Assisted Surgery, vol. 4, No. 3, pp. 202-209, Jun. 19, 2008.
Anonymous: "Inraoperative Structure Update—Brainlab User Guides", pp. 1-2, Jan. 18, 2018.

* cited by examiner

*Primary Examiner* — Katrina M Stransky
(74) *Attorney, Agent, or Firm* — Harness Dickey (57) ABSTRACT

Disclosed is a method and system for performing a procedure. The system may include a navigation system to be used to at least assist in the procedure. The system may assist in delineating objects and/or determining physical characteristics of subject portions. The system may assist in performing and/or a workflow of the procedure.

24 Claims, 6 Drawing Sheets

SYSTEM AND METHOD FOR PERFORMING AND EVALUATING A PROCEDURE

FIELD

The subject disclosure relates generally to a system and method for determining a position, including location and orientation, of a member in space relative to a subject.

BACKGROUND

This section provides background information related to the present disclosure which is not necessarily prior art.

Various procedures may be selected to repair or replace portions of selected subjects. For example, in a human subject a portion of the human anatomy may be selected to be repaired or replaced. During the procedure, a minimally or low invasive procedure may be selected. The low invasive procedure may limit direct viewing of a work area within the subject, but may decrease recovery time and/or discomfort to the subject.

A navigation system for various procedures, such as surgical procedures, assembling procedures, and the like, allow an instrument or object to be tracked. Tracking systems may include appropriate tracking systems, such as optical, acoustic, electro-magnetic (EM), etc. EM tracking or navigation systems include the AxiEM™ electro-magnetic navigation system sold by Medtronic Navigation, Inc., having a place of business in Louisville, Colo. The AxiEM™ electro-magnetic navigation system may include a plurality of coils that are used to generate an electromagnetic field that is sensed by a tracking device, which may be the sensor coil, to allow a navigation system, such as a StealthStation® surgical navigation system, to be used to track and/or illustrate a tracked position of an instrument. Optical tracking systems include those such as the Stealth-Station® S7® tracking system. The optical tracking system includes a set of cameras with a field of vision to triangulate a position of the instrument.

SUMMARY

This section provides a general summary of the disclosure, and is not a comprehensive disclosure of its full scope or all of its features.

A tracking device connected to an instrument is generally required to allow tracking and navigation of the instrument. The instrument, therefore, is generally specific to a tracking or navigation system. A user specific instrument, such as surgeon specific instrument may not include a tracking device. Disclosed is an auxiliary instrument that may be tracked and a tracking and/or navigation system that may be used with the auxiliary system to track a progress or extent of a procedure.

A system for performing a procedure is disclosed. The procedure may also be performed on a living subject such as an animal, human, or other selected patient. The procedure may include any appropriate type of procedure, such as one being performed on an inanimate object (e.g. an enclosed structure, airframe, chassis, etc.). Nevertheless, the procedure may be performed using a navigation system where a tracking system is able to track a selected one or more items.

A navigation system may be used to navigate an instrument relative to a subject during a selected portion of a procedure. In various embodiments, the procedure may include a procedure on a spine such as a spinal fusion (i.e. two or more vertebrae are connected together with a selected implant system or assembly) and/or discectomy. During a discectomy portion of the procedure, the removal tool (e.g. a curette) may not include a tracking device. Thus, the cutting or removal instrument may not be directly tracked and/or navigated. An auxiliary or volume checking tool may include a tracking device to allow the auxiliary instrument to be tracked and/or navigated.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
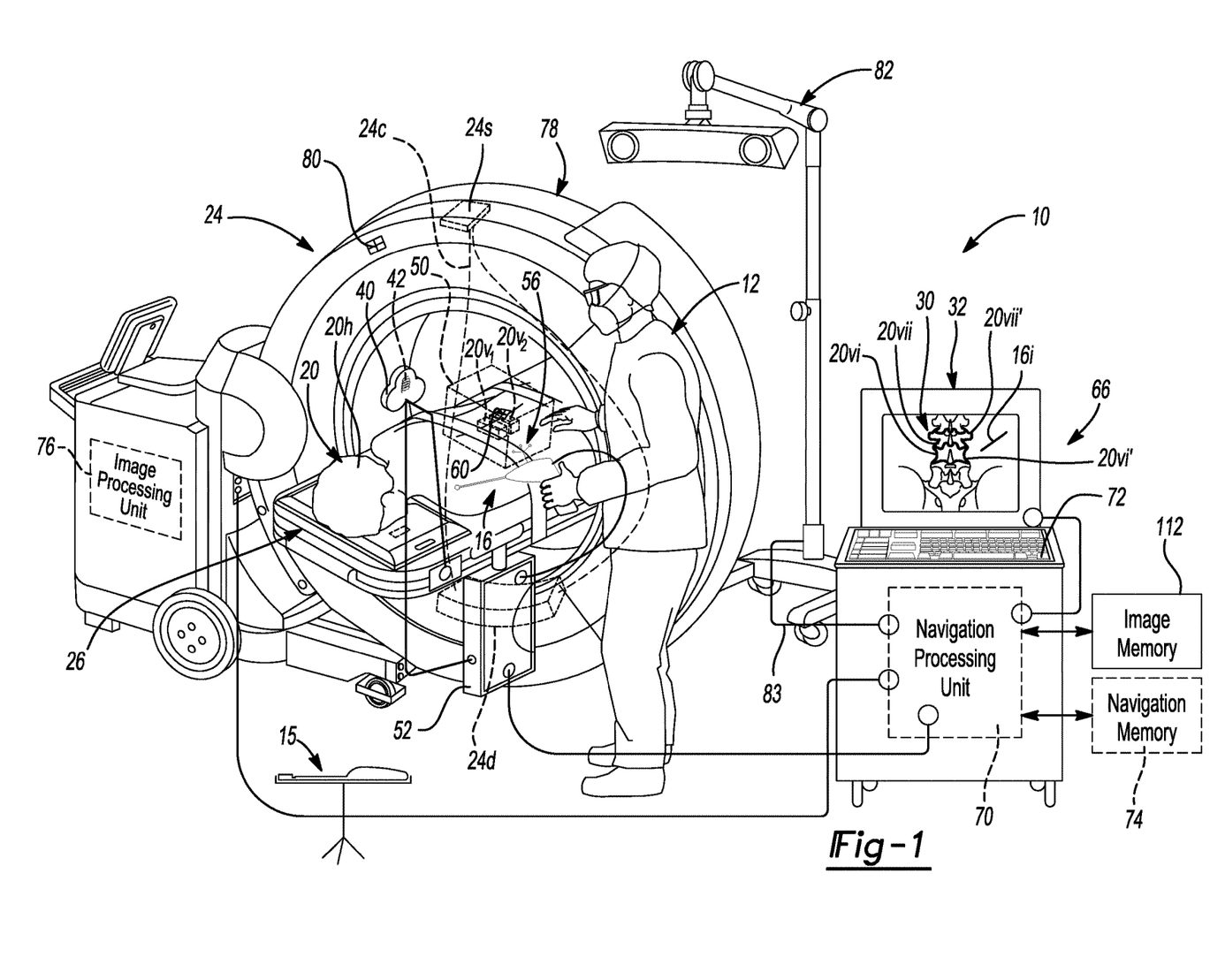
FIG. 1 is an environmental view of an operating suite including a navigation system, according to various embodiments.

With initial reference to FIG. 1, a navigation system 10 is illustrated. The navigation system 10 may be used for various purposes or procedures by one or more users, such as a user 12. The navigation system 10 may be used to determine or track a position of an instrument 16 in a volume. The position may include both a three dimensional X,Y,Z location and orientation. Orientation may include one or more degree of freedom, such as three degrees of freedom. It is understood, however, that any appropriate degree of freedom position information, such as up to or less than six-degree of freedom position information, may be determined and/or presented to the user 12.

Tracking the position of the instrument 16 may assist the user 12 in determining a position of the instrument 16, even if the instrument 16 is not directly viewable by the user 12. Various procedures may block the view of the user 12, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject 20 and the procedure may be performed on the human subject 20.

It is understood, however, that the instrument 16 may be tracked and/or navigated relative to any subject for any appropriate procedure. Tracking or navigating an instrument for a procedure, such as a surgical procedure, on a human or living subject is merely exemplary. Further, an initial or selected portion of the procedure may occur with an instrument, such as a first instrument 15 that is not tracked or may not be navigated. The non-tracked instrument 15 may be used for selected portions of the procedure, such as a resection or cutting. Thus, in various embodiments only the instrument 16, which may be referred to as a second or auxiliary instrument, may be tracked and have a tracked device associated (e.g. attached) therewith. The first instrument 15 may not be tracked or navigated and may not have a tracking device associated therewith.

Nevertheless, in various embodiments, the surgical navigation system 10, as discussed further herein, may incorporate various portions or systems, such as those disclosed in U.S. Pat. Nos. RE44,305; 7,697,972; 8,644,907; and 8,842,893; and U.S. Pat. App. Pub. No. 2004/0199072, all incorporated herein by reference. Various components that may be used with or as a component of the surgical navigation system 10 may include an imaging system 24 that is operable to image the subject 20, such as an O-arm® imaging system, magnetic resonance imaging (MRI) system, computed tomography system, etc. A subject support 26 may be used to support or hold the subject 20 during imaging and/or during a procedure. The same or different supports may be used for different portions of a procedure.

In various embodiments, the imaging system 24 may include a source 24s. The source 24s may emit and/or generate X-rays. The X-rays may form a cone 24c, such as in a cone beam, that impinge on the subject 20. Some of the X-rays pass though and some are attenuated by the subject 20. The imaging system 24 may further include a detector 24d to detect the X-rays that are not completely attenuated, or blocked, by the subject 20. Thus, the image data may include X-ray image data. Further, the image data may be two-dimensional (2D) image data.

Image data may be acquired, such as with one or more of the imaging systems discussed above, during a surgical procedure or acquired prior to a surgical procedure for displaying an image 30 on a display device 32. In various embodiments, the acquired image data may also be used to form or reconstruct selected types of image data, such as three-dimensional volumes, even if the image data is 2D image data.

The trackable instrument 16 may be tracked in a trackable volume or a navigational volume by one or more tracking systems. Tracking systems may include one or more tracking systems that operate in an identical manner or more and/or different manner or mode. For example, the tracking system may include an electro-magnetic (EM) localizer 40, as illustrated in FIG. 1. In various embodiments, it is understood by one skilled in the art, that other appropriate tracking systems may be used including optical, radar, ultrasonic, etc. For example, an optical localizer 82 may be used to track the instrument 16.

The discussion herein of the EM localizer 40 and tracking system is merely exemplary of tracking systems operable with the navigation system 10. The position of the instrument 16 may be tracked in the tracking volume relative to the subject 20. The position, or selected portion of the instrument 16, may then be illustrated as a graphical representation, also referred to as an icon, 16i with the display device 32. In various embodiments, the icon 16i may be superimposed on the image 30 and/or adjacent to the image 30. As discussed herein, the navigation system 10 may incorporate the display device 32 and operate to render the image 30 from selected image data, display the image 30, determine the position of the instrument 16, determine the position of the icon 16i, etc.

With reference to FIG. 1, the EM localizer 40 is operable to generate electro-magnetic fields with a transmitting coil array (TCA) 42 which is incorporated into the localizer 40. The TCA 42 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the coils 42 and form a navigation domain or volume 50, such as encompassing all or a portion of a head 20h, spinal vertebrae 20v, or other appropriate portion. The coils may be powered through a TCA controller and/or power supply 52. It is understood, however, that more than one of the EM localizers 40 may be provided and each may be placed at different and selected locations.

The navigation domain or volume 50 generally defines a navigation space or patient space. As is generally understood in the art, the instrument 16, such as a probe, may be tracked in the navigation space that is defined by a navigation domain relative to a patient or subject 20 with an instrument tracking device 56. For example, the instrument 16 may be freely moveable, such as by the user 12, relative to a dynamic reference frame (DRF) or patient reference frame tracker 60 that is fixed relative to the subject 20. Both the tracking devices 56, 60 may include tracking portions that are tracked with appropriate tracking systems, such as sensing coils (e.g. conductive material formed or placed in a coil) that senses and are used to measure a magnetic field strength, optical reflectors, ultrasonic emitters, etc. Due to the tracking device 56 connected or associated with the instrument 16, relative to the DRF 60, the navigation system 10 may be used to determine the position of the instrument 16 relative to the DRF 60.

The navigation volume or patient space may be registered to an image space defined by the image 30 of the subject 20 and the icon 16i representing the instrument 16 may be illustrated at a navigated (e.g. determined) and tracked position with the display device 32, such as superimposed on the image 30. Registration of the patient space to the image space and determining a position of a tracking device, such as with the tracking device 56, relative to a DRF, such as the DRF 60, may be performed as generally known in the art, including as disclosed in U.S. Pat. Nos. RE44,305; 7,697,972; 8,644,907; and 8,842,893; and U.S. Pat. App. Pub. No. 2004/0199072, all incorporated herein by reference.

The navigation system 10 may further include and or be in communication with a navigation processor system 66. The navigation processor system 66 may include connections to the display device 32, the TCA 40, the TCA controller 52, and other portions and/or connections thereto. For example, a wire connection may be provided between the TCA controller 52 and a navigation processing unit 70. It is understood that the navigation processing unit 70 may include one or more processors of various types (e.g. general purpose processors executing accessed instructions and/or specific processors (e.g. ASIC)). Further, the navigation processor system 66 may have one or more user control inputs, such as a keyboard 72, and/or have additional inputs such as from communication with one or more memory systems 74, either integrated or via a communication system. The navigation processor system 66 may, according to various embodiments include those disclosed in U.S. Pat. Nos. RE44,305; 7,697,972; 8,644,907; and 8,842,893; and U.S. Pat. App. Pub. No. 2004/0199072, all incorporated herein by reference, or may also include the commercially available StealthStation® or Fusion™ surgical navigation systems sold by Medtronic Navigation, Inc. having a place of business in Louisville, Colo.

Tracking information, including information regarding the magnetic fields sensed with the tracking devices 56, 60, may be delivered via a communication system, such as the TCA controller, which also may be a tracking device controller 52, to the navigation processor system 66 including the navigation processor 70. Thus, the tracked position of the instrument 16 may be illustrated as the icon 16$i$ relative to the image 30. Various other memory and processing systems may also be provided with and/or in communication with the processor system 66, including the memory system 72 that is in communication with the navigation processor 70 and/or an imaging processing unit 76.

The image processing unit 76 may be incorporated into the imaging system 24, such as the O-arm® imaging system, as discussed above. The imaging system 24 may, therefore, including the various portions such as a source and a x-ray detector that are moveable within a gantry 78. The imaging system 24 may also be tracked with a tracking device 80. It is understood, however, that the imaging system 24 need not be present while tracking the tracking devices, including the instrument tracking device 56. Also, the imaging system 24 may be any appropriate imaging system including a MRI, CT, etc.

In various embodiments, the tracking system may include an optical localizer 82. The optical localizer 82 may include one or more cameras that view or have a field of view that defines or encompasses the navigation volume 50. The optical localizer 82 may receive light (e.g. infrared or ultraviolet) input to determine a position or track the tracking device, such as the instrument tracking device 56. For example, at least two cameras at a fixed position relative to one another may view both the tracking device 56 of the instrument 16 and the DRF 60 on the patient 20. Due to registration, the tracking system and the navigation system 10 may then determine the position of the instrument 16 (including at least a portion thereof) relative to the subject 20. Generally, the position may be triangulated using the view of the volume 50. It is understood that the optical localizer 82 may be used in conjunction with and/or alternatively to the EM localizer 40 for tracking the instrument 16 and may also have a communication line 83 with the navigation processor system 66.

Information from all of the tracking devices may be communicated to the navigation processor 70 for determining a position of the tracked portions relative to each other and/or for localizing the instrument 16 relative to the image 30. The processor 70 may execute instructions or be designed to analyze the incoming navigation signals to determine the position of the instrument 16, as is generally understood in the art as discussed above. The determined position of the instrument 16, however, may be displayed with the display device 32 in various manners and with various indications, as discussed herein. The imaging system 24 may be used to acquire image data to generate or produce the image 30 of the subject 20. It is understood, however, that other appropriate imaging systems may also be used. The TCA controller 52 may be used to operate and power the EM localizer 40, as discussed above.

The image 30 that is displayed with the display device 32 may be based upon image data that is acquired of the subject 20 in various manners. For example, the imaging system 24 may be used to acquire image data that is used to generate the image 30. It is understood, however, that other appropriate imaging systems may be used to generate the image 30 using image data acquired with the selected imaging system. Imaging systems may include magnetic resonance imagers, computed tomography imagers, and other appropriate imaging systems. Further, the image data acquired may be two dimensional or three dimensional data and may have a time varying component, such as imaging the patient during a heart rhythm and/or breathing cycle.

In various embodiments, the image data is a 2D image data that is generated with a cone beam. The cone beam that is used to generate the 2D image data may be part of an imaging system, such as the O-arm® imaging system. The 2D image data may then be used to reconstruct a 3D image or model of the imaged subject, such as the patient 20. The reconstructed 3D image and/or an image based on the 2D image data may be displayed. Thus, it is understood by one skilled in the art that the image 30 may be generated using the selected image data.

Further, the icon 16$i$, determined as a tracked position of the instrument 16, may be displayed on the display device 32 relative to the image 30. In addition, the image 30 may be segmented, for various purposes, including those discussed further herein. Segmentation of the image 30 may be used to determine and/or delineate objects or portions in the image. In various embodiments, the delineation may be used to identify boundaries of various portions within the image 30, such as boundaries of one or more structures of the patient that is imaged, such as the vertebrae 20$v$. Accordingly, the image 30 may include an image of one or more of the vertebrae 20$v$, such as a first vertebra 20$vi$ and a second vertebra 20$vii$. In various embodiments, the delineation may be represented, such as with selected icons, such as an icon 20$vi'$ or a second icon 20$vii'$. The boundaries 20$vi'$, 20$vii'$ may be determined in an appropriate manner and for various purposes, as also discussed further herein. Selected anatomical portions may include displaying a disc between vertebrae and or determining that a disc is between determined vertebrae. For example, in various imaging modalities, soft tissue of a disc may not be easily or directly viewable, while the bone of the vertebrae is easily viewed by the user 12.

With continuing reference to FIG. 1, the subject 20 may include a plurality of vertebrae, such as a first vertebra 20$v_1$ and a second vertebra 20$v_2$. The vertebrae 20$v$ may be surrounded or covered by soft tissue, such as a dermis, muscle, and the like. In performing a selected procedure, such as in a spinal fusion, discectomy, or other procedures, a small incision 230 (FIG. 2) may be made. A small incision may allow for a substantially minimal or low invasive procedure. For example, the incision may generally be about 1 millimeter (mm) to about 3 centimeters (cm) in length. Generally the incision allows access for instruments, such as the first instrument 15 or the second or auxiliary instrument 16 to a selected area while minimizing the incision size, which may also limit the view of the user 12 of the area where a procedure is occurring. In various procedures, such as in a spinal fusion, a discectomy may occur. A discectomy may include removing a portion or all of a disc. The disc may generally be the tissue between two vertebrae, such as the vertebrae 20$v_1$ and 20$v_2$. The two vertebrae may be any appropriate vertebrae, such as a third lumbar vertebra ($L_3$) and a fourth lumbar vertebra ($L_4$).

As illustrated in FIG. 1, the image 30 may include the vertebrae of the subject, along with other tissue of the subject 20. As discussed further herein, an illustration of the vertebrae may include the image acquired with the imaging system 24, or any appropriate imaging system, or a selected reconstruction thereof, such as a three-dimensional reconstruction.

In various embodiments, the imaging system 24, or any appropriate imaging system, may include an image processing unit 76 that may be used to analyze and allow for manipulation of selected images. The images may be stored with the imaging system 24 and/or stored in a selected image memory 112. Further, various instructions such as tracking, registration, and the like may be stored in the navigation memory 74.

According to various embodiments, the user 12 may plan or select a selected procedure for the subject 20. In planning the procedure, the user 12 may predetermine or preselect a volume of the anatomy to be manipulated. In various embodiments the user 12 may predetermine a volume of the disc to be removed between the vertebrae $20v_1$ and $20v_2$. For example, the user 12 may select to remove about 10% to about 90%, including further about 30% to about 80%, and further including about 60% to about 80%. Generally, the user 12 may select to remove a substantially central or middle portion of the disc between adjacent vertebrae. The user 12 may select to maintain a selected portion of the disc, such as an annulus of the disc, to assist in maintaining an implant (e.g. intervertebral implant and/or bone graph). Accordingly, the user may predetermine an amount of volume to be removed.

With use of the image 30 and the display device 32, the user 12 may also specifically identify a region or volume to be removed. As discussed above, selected vertebrae may be displayed $20vi$ and $20vii$. Icons may be used to represent the vertebrae, such as being delineated or identified by the user 12. The vertebrae icons $20vi'$ and $20vii'$ may be used by the navigation processing unit 70, or any appropriate processing unit, such as a planning processing unit, to assist in determining a volume between the two vertebrae $20v_1$ and $20v_2$ displayed in the image 30. The user 12 may specifically define a volume or portion of the volume of the disc to be removed between the selected vertebrae in the image 30. For example, the user 12 may use selected inputs, such as the input 72, to identify the volume to be removed. In various embodiments, the user 12 may identify a selected volume such as about 2 cubic centimeters (cc) to about 8 cc, and further including about 4 cc to about 6 cc.

The user may define a volume, such as with an icon or template, and place the template adjacent to the image 30. The navigation system 66 may then determine a position of the tracked instrument 16 relative to the predetermined volume displayed with the display device 32 relative to the image 30. Moreover, as discussed further herein, the navigation system 66 may be used to determine a volume identified by the tracked instrument 16 when the tracked instrument 16 is moved within the navigated volume 50.

Figure 2:
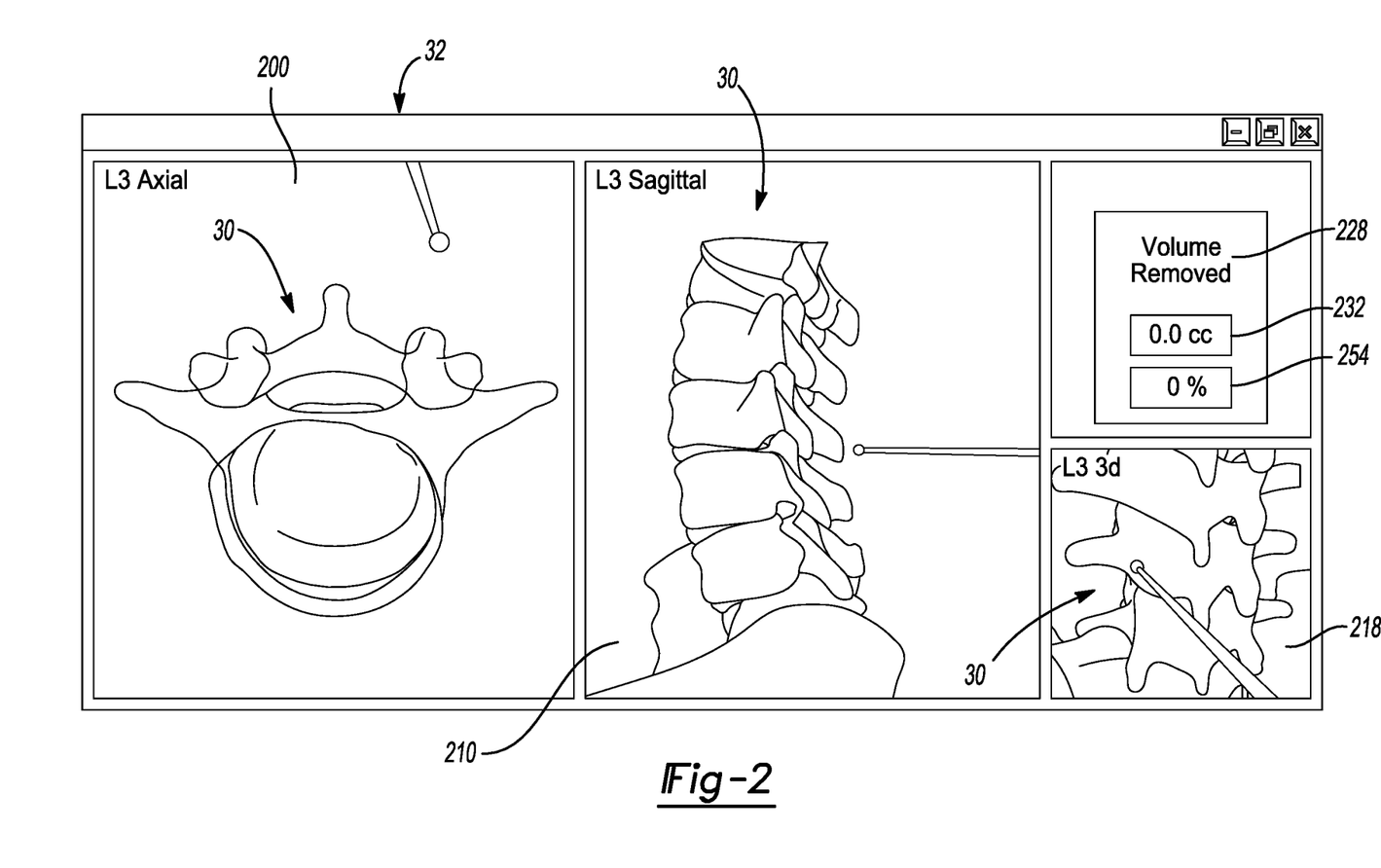
FIG. 2 is an illustration of a screen including images of a spine of a patient with no volume information.

With continuing reference to FIG. 1 and further reference to FIG. 2, the display device 32 may display one or more images of the subject 20. For example, the display device 32 may display a plurality of windows including an axial view window 200, a sagittal view window 210 and a 3D view window 218. Each of the views in the windows 200, 210, 218 may be viewed by the user 12 substantially simultaneously with the display device 32. The user 12 may also select which views to be viewed on the display device 32 and the view windows 200, 210, 218 are merely exemplary. Further, additional information may also be displayed for view by the user 12 such as a volume removed window 226. The volume removed window 226 may include a title 228, such as Volume Remove (or any appropriate title), an absolute numerical volume box 232, and/or a percentage removed box 254. At the initiation of a procedure the numerical value box 232 may illustrate or identify 0.0 cc and 0%. Accordingly, the user 12 may view the indication that no determined volume has been removed from the subject 20.

Figure 3A:
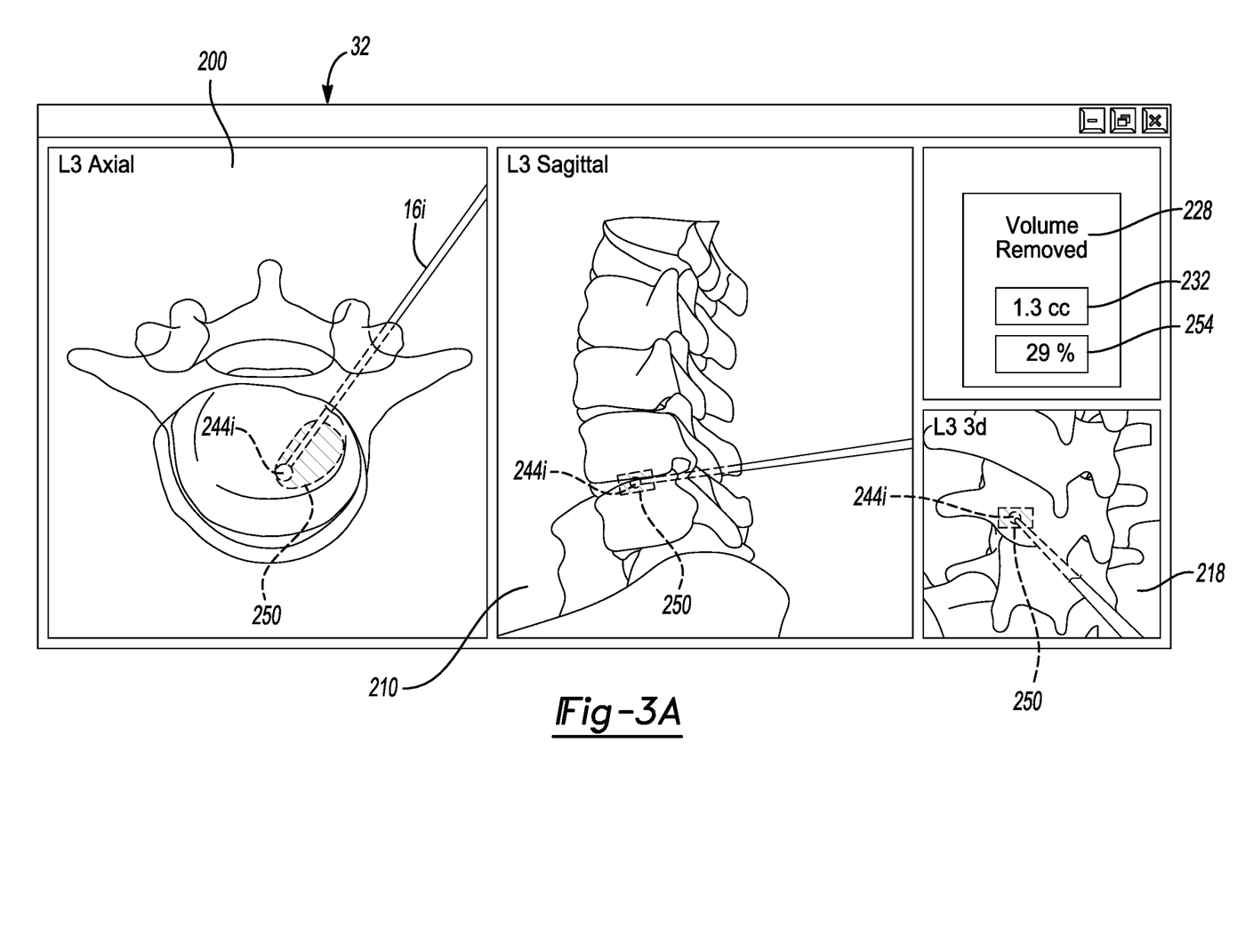
FIG. 3A is an illustration of a screen including images of a spine of a patient with volume tracking information.
Figure 3B:
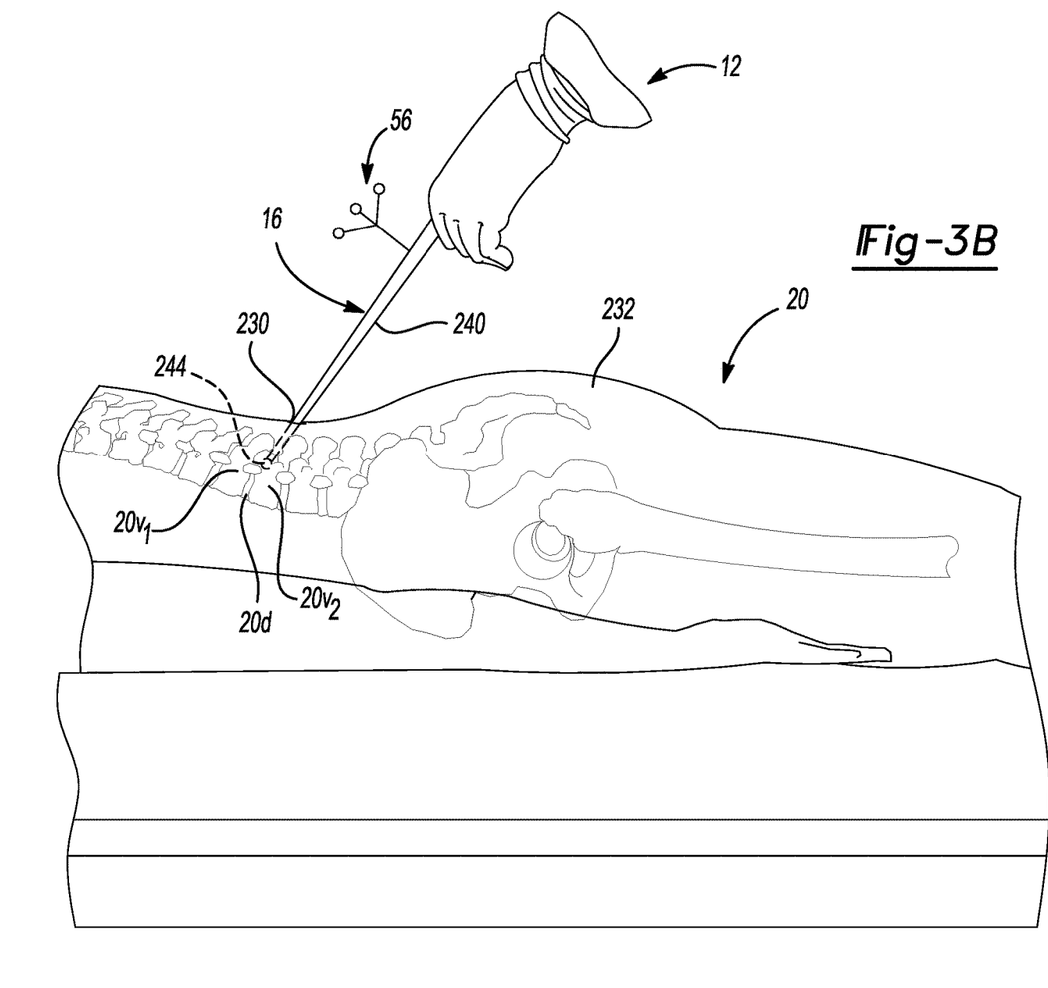
FIG. 3B is a detailed environmental view of a tracked auxiliary or second instrument within a subject.

Turning reference to FIG. 3A and FIG. 3B, the display device 32 may display a tracked or navigated location of the instrument 16 as the icon 16i. The instrument 16 may be tracked as it is moved relative to the subject 20. For example, the user 12 may position the instrument 16 through an incision 230. The incision 230 may be initially produced to allow positioning the instrument 15 into the subject 20 for performing an initial portion of the procedure. The instrument 15 may be a non-navigated or non-tracked instrument that may be used to cut or resect tissue. For example, during a discectomy, tissue may be removed from the disc between the vertebrae $20v_1$ and $20v_2$. A disc or disc space $20d$ may be the disc of the subject 20 between the two vertebrae $20v_1$ and $20v_2$. During removal of tissue from the disc $20d$, a void may be formed in the disc space $20d$. A cutting or tissue removal instrument may not be tracked or navigated to allow for viewing or determining the position of the resected material. Resecting material with a navigated instrument, however, is disclosed in U.S. Pat. No. 7,542,791, issued Jun. 2, 2009, incorporated herein by reference.

When the instrument 15 is not navigated or tracked and the incision 230 is of a selected size such that the user 12 does not have direct view of the disc space $20d$, the tracked instrument 16 may be moved into the disc space $20d$. The instrument 15 that is not tracked, in various embodiments, may be the only instrument that cuts or removes material form the subject 20. Moving the tracked instrument 16 into the disc space $20d$ allows for a determination or visualization of the volume resected with the instrument 15 using the display device 32. The tracked instrument 16, therefore, may only be moved and not cut or remove tissue or material from the subject 20. As discussed herein, the instrument 16 may be moved within the disc space $20d$ to indicate the volume resected or removed with the instrument 15.

The instrument 16 may include the trackable member 56 that is tracked with a selected tracking system, such as the optical localizer 82. The instrument 16 may further include a shaft or elongated member 240 that ends in a distal end or tip 244. The distal tip 244 may include a selected geometry, such as a substantially spherical member positioned at the end of the elongated member 240. The distal end 244, however, may be any appropriate shape or geometry such as ovoid, curved, cylindrical, ellipsoid, etc. In various embodiments, for example when the distal end is substantially spherical or forms at least a portion of a sphere, the distal end 244 may have a selected radius $244r$ that extends from a center to a surface $244s$ (FIG. 4B). The surface $244s$ may be a substantially smooth or non-abrasive or non-cutting surface, such that it may contact a resected surface within the disc space $20d$. Further, the geometry or volume of the distal end 244 may be known, such as saved in the memory 74 so that its tracked movement within the disc space $20d$ may be used to determine a volume of a void within the disc space $20d$. Again the void into which the instrument 16 is placed may be formed by the instrument 15 that is not tracked.

The tracked instrument 16 may be moved through the void and a painted or illustrated volume or area 250 may be illustrated on the display device 32 relative to the different view windows 200, 210, 218. In each of the view windows the volume 250 may be illustrated to display the volume through which the tracked instrument 16, including the distal end 244 thereof, has moved. Accordingly, the display device 32 may display graphical illustration of a volume through which the distal end 244 has moved. As discussed herein, the volume 250 is "painted", substantially or only, as selected, by tracking movement of the tracking device 56 and the known position of the distal end 244 relative thereto. Further, the icon 16*i* may illustrate the instrument, including the distal end 244*i*.

The information window may illustrate the volume removed by a numerical value 232, such as 1.3 cc. Further, as discussed above, a predetermined or preselected volume may be made by the user 12 to be resected. The predetermined volume may be saved in the navigation memory 74. Accordingly, the processor system 66, including the processor 70, may determine the percentage or fraction of the determined volume as a portion of the hole. Accordingly, the portion of the whole predetermined volume may also be displayed, such as 29%.

The user 12 may view the determined volume graphically, numerically as an absolute value, or numerically as a percent, or any other appropriate manner in determining whether more resection is selected. If more resection is selected, the user 12 may withdraw the tracked instrument 16 and position the non-tracked instrument 15 within the disc space 20*d* to continue resection and removal of tissue therefrom. After a selected amount of time or movement of the instrument 15, the user 12 may then reinsert the tracked instrument 16 to move within the void formed by removing of tissue. This process may continue until the user has determined that a selected amount of tissue has been removed. Generally, the instrument 15 is first removed prior to placing the tracked instrument through the incision 230 into the created void.

Figure 4A:
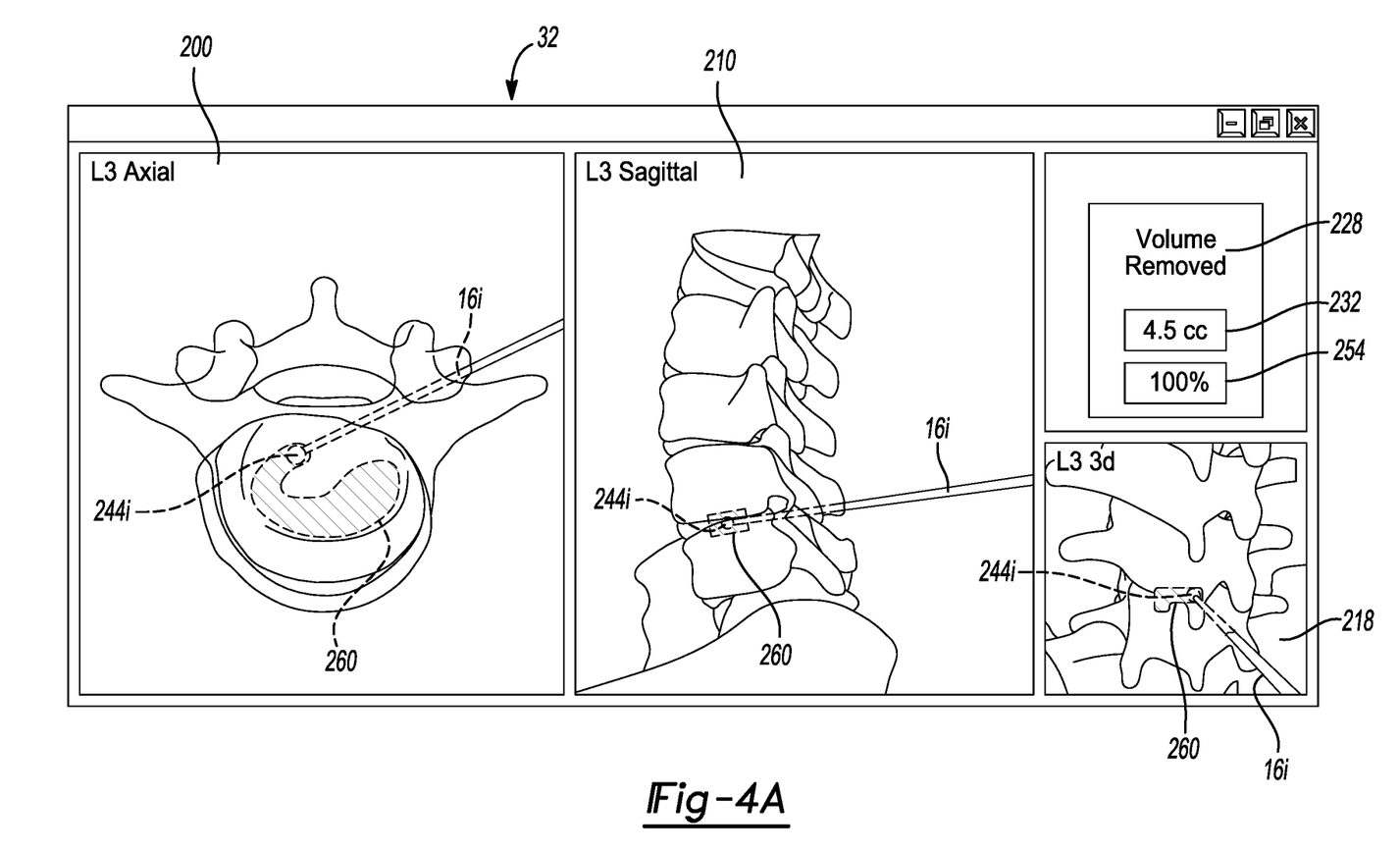
FIG. 4A is an illustration of a screen including images of a spine of a patient with further volume tracking information.
Figure 4B:
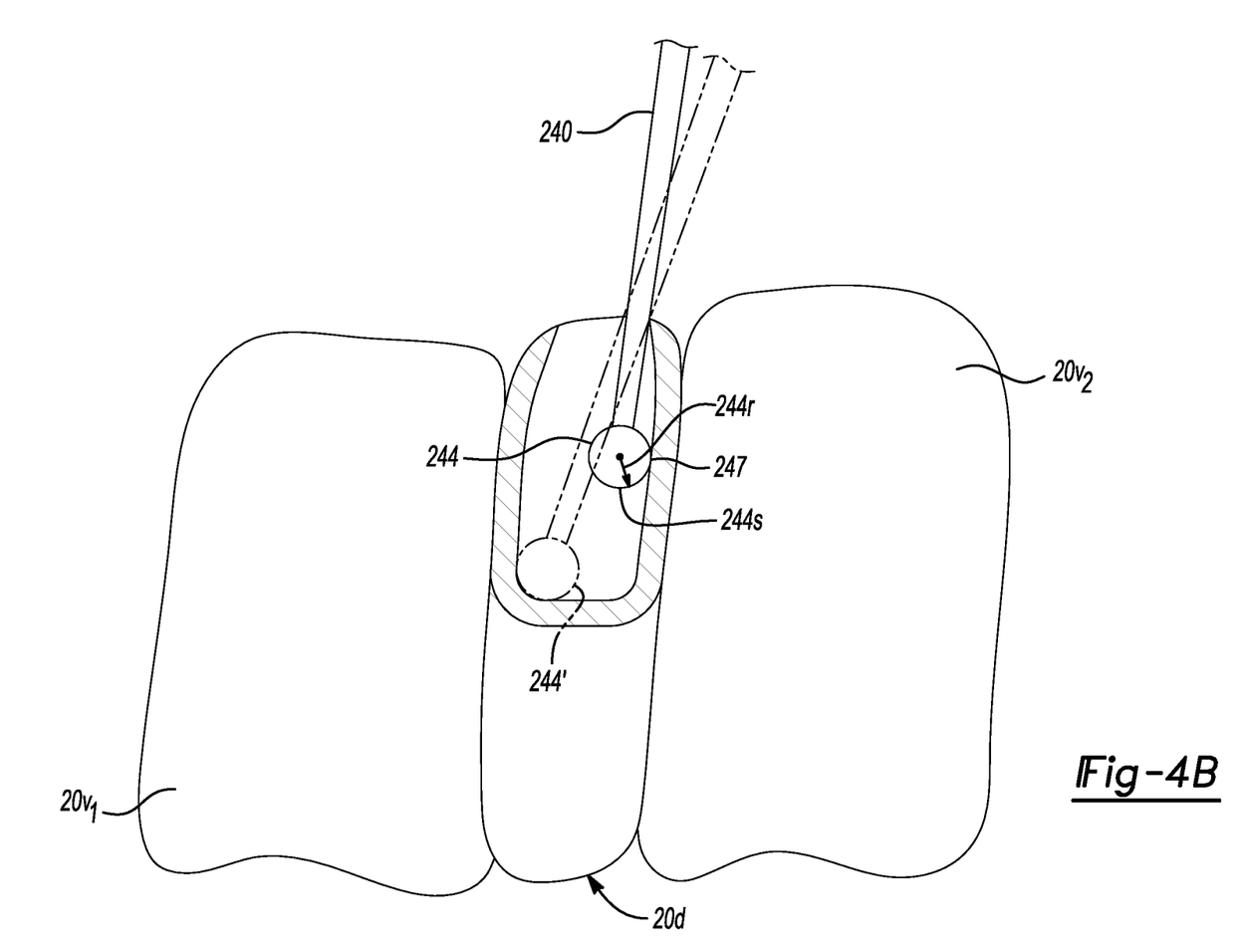
FIG. 4B is a detailed environmental view of a tracked auxiliary or second instrument within a subject.

With reference to FIG. 4A and FIG. 4B, the display device 32 may display the tracked instrument icon 16*i* including the tip 24*i* thereof and a second volume 260. The second volume 260 may also be viewed or displayed in each of the view windows 200, 210, 218. The second volume 260 may be based upon further movement of the tracked instrument 16 within the disc space 20*d*. As illustrated in FIG. 4B, the tracked instrument 16 may be moved from a first position to a second position 244' (illustrated in phantom). Movement of the tracked instrument 16 may allow for a real time display of the volume 260, such as if the user 12 were paining the volume.

When moving the tracked instrument 16, which may only include a smooth surface 244*s*, the painting of the volume 260 may occur. In painting the display 32 may display the volume 260 with a selected color. The color may change from a first to a second color to indicate that the distal end 244 has already been tracked in an area or volume. Thus, the user 12 may more efficiently move the distal end 244 to all portions or areas of the void. Generally, the determined volume may only be of the volume in which the instrument 16, which is tracked, is moved. Thus, the user 12 may also be prompted to confirm movement to all areas in the void of the disc space 20*d*. Further, the user 12 may ensure that the void is all a second color to confirm that the instrument 16 has moved within the area or volume at least twice for a confirmation.

The second volume 260 may be any appropriate volume following the first volume measured with the tracked instrument 16. As illustrated in FIG. 4A, for example, the volume removed may be identified as the absolute value 4.5 cc in the value box 232. Further in the percent or portion box 254, 100% may be displayed. Accordingly, the user may be notified that the volume removed is equal to the predetermined volume to be removed, such as by comparison to a recalled predetermined volume from the navigation memory 74.

With reference to FIG. 4B, during movement of the instrument 16 within the disc space 20*d*, the display device 32 may, in real time, such as substantially with movement or in time with movement of the tracked instrument 16, illustrate the second volume 260, or any selected series of volume. Accordingly, the user 16 may move the tracked instrument 16 within the disc space 20*d* and view a real time movement or painting of the volume determined or measured by a tracking instrument 16 within the disc space 20*d*. Thus, the user 12 may view in real time the volume of a void created within the disc space 20*d* during a selected procedure, such as a discectomy.

The volume is determined by tracking the distal end 244 throughout its movement within the disc space 20*d*. Generally, the user 12 moves the distal end along all of the surfaces within the disc space 20*d* and within the open volume in the disc space 20*d*. By adding the non-overlapping positions of the distal end 244, a volume is determined. The volume of the distal end 244 is known based on its geometry and dimensions, such as the radius of the sphere.

The volume may be determined by the navigation system 10, such as by the processor unit 70 executing instructions to add the non-overlapping volumes together. The navigation system 10 may, therefore, substantially automatically determine the volume 250, 260 or any appropriate volume with the tracked instrument 16. The determined volume is then displayed, as discussed above.

Once the user 12 has determined an appropriate amount of disc has been removed and a selected volume of space when the disc has been created the user 12 may perform additional procedural steps. For example, the user 12 may pack the void with a selected material, such as a bone graft. In various embodiments, a cage may also be positioned within the volume that is either filled or packed with a selected graph or bone graph. The cage may include a cage such as an Inter Fix™ Threaded spinal Fusion Device, sold by Medtronic, Inc. It is understood, however, that any appropriate procedure may follow.

Further, it is understood that the instrument 16 may be used to track or determine a volume in any appropriate portion of a subject. For example, during a tumor removal, such as a resection of a cancerous tumor in various portions of the anatomy including the brain, near a spinal column, or the like, a non-navigated instrument may be used during resection or removal. Further, other selected portions of the anatomy may be analyzed for volume, such as a sinus cavity, nasal passage, ear canal, etc.

The tracked instrument 16 may be positioned within the subject using the same incision for the resection instrument and the tracked instrument may be moved within the created void. Tracking the tracked instrument in the created void may be used to determine the volume of the created void even if the resection instrument is not tracked. Accordingly the second or auxiliary instrument 16 that is tracked may be used to determine a volume or an area that is resected with a non-navigated instrument. Thus the user 12 may use selected instruments, such as procedure specific instruments, user specific instruments, or other appropriate instruments for performing a procedure while allowing for determination of a volume or area based upon a tracked location of an auxiliary or secondary instrument.

Further, it is understood that the user 12 may determine and/or the navigation system 10 may automatically determine when and/or where to begin or include in the volume determination. For example, the user 12 may provide an input to begin volume determination and/or painting once the user 12 views that the distal end 244 is within the volume of the disc space 20d due to registration of the image 30 to the subject 20. Alternatively, or in addition thereto, the navigation system 10 may determine automatically to initiate volume determination based on the tracked position of the distal end 244 at or near the disc space 20d.

Similarly, the painting of the volume determination may be substantially coincident with the initiation of the volume determination or at some other time. Generally, however, the painting of the volume for viewing by the user 20 will be initiated with volume determination initiation to determine and illustrate a selected volume or space, such as a resected disc space. Generally, however, the instrument 16 and the distal end 244 thereof is tracked and navigated, whether or not the determination of a volume or space has been initiated and/or painting of the determined volume and/or area.

It is further understood that the user 12 may select to operate the navigation system 10 for various purposes. For example, the user 12 may view a calculated volume based on the tracked position of the distal end 244, for example a discrete calculated volume such as 4 cc. The user 12 may also, or alternatively, select to have displayed and/or determined a percentage of a predetermined volume, such as 45%. The user 12 may also or alternatively selected to display the painted volume, such as the volume 260 or any volume through which the distal end 244 has been moved and tracked. The user 12 may selected to have only one, only two, or all three of the above or any appropriate representation of the volume through which the tracked instrument 16, including the distal end 244, has been tracked.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of performing a procedure, comprising:
   preparing a subject;
   gaining access to a portion of the subject with a non-tracked instrument;
   removing a first portion of the portion of the subject with the non-tracked instrument;
   gaining access to the portion of the subject with a tracked instrument;
   moving at least a first instrument portion of the tracked instrument within the first portion of the portion of the subject;
   tracking the tracked instrument within the first portion of the portion of the subject while moving at least the first instrument portion; and
   determining a representation of the first portion based on the tracking the tracked instrument within the first portion of the portion of the subject while moving at least the first instrument portion.

2. The method of claim 1, further comprising:
   predetermining a volume to remove from the subject prior to gaining access to the portion of the subject with the non-tracked instrument.

3. The method of claim 2, wherein the planned volume includes a volume of a spinal disc to remove during a discectomy.

4. The method of claim 2, wherein gaining access to the portion of the subject with the non-tracked instrument includes moving a cutting instrument into the first portion.

5. The method of claim 4, wherein gaining access to the portion of the subject with the tracked instrument including moving the first instrument portion including a distal tip of the tracked instrument into the first portion, wherein the distal tip includes a substantially non-cutting end.

6. The method of claim 5, further comprising:
   determining a trackable surface of the distal end;
   wherein moving at least the first instrument portion of the tracked instrument within the first portion of the portion of the subject includes moving the distal tip within the first portion; and
   wherein tracking the tracked instrument within the first portion of the portion of the subject while moving at least the first instrument portion includes tracking the determined trackable surface of the distal end.

7. The method of claim 6, wherein determining the representation of the first portion based on the tracking the tracked instrument within the first portion of the portion of the subject while moving at least the first instrument portion includes:
   operating a processor system to execute instructions to determine a volume through which the distal tip has passed; and
   displaying the determined volume with a display device.

8. The method of claim 7, wherein displaying the determined volume with the display device includes displaying a representation of an amount of the predetermined volume removed from the subject.

9. The method of claim 7, wherein displaying the determined volume with the display device includes displaying a first color with the display device to illustrate a first volume through which the distal tip has been moved and displaying a second color with the display device to illustrate a second volume through which the distal tip has not been moved.

10. The method of claim 9, wherein the second color is an image representation color and the first color is different from the image representation color.

11. The method of claim 9, further comprising:
    updating the illustration to display the first color in real time as the tracked instrument is moved within the first portion.

12. The method of claim 7, wherein displaying the determined volume with the display device includes displaying a value of the volume of the first portion.

13. A method of performing a procedure, comprising:
    preparing a subject;

gaining access to a disc space within a spinal column of the subject with a first instrument;
removing a first portion of a disc in the disc space of the subject with the first instrument;
gaining access to the first portion of the disc space with at least a distal end of a second instrument after removing the first portion of the disc in the disc space of the subject with the first instrument;
moving the distal end of the second instrument within the first portion of the disc space of the subject;
tracking the second instrument within the first portion of the disc space of the subject while moving at least the distal end of the second instrument; and
executing instructions with a processor system for:
 determining a volume of the first portion based on the tracking the second instrument within the first portion of the disc space of the subject while moving at least the distal end of the second instrument,
 displaying a representation of the determined volume with a display device,
 wherein displaying the determined volume with the display device includes illustrating a first volume through which the distal end has been move with a first color and illustrating a second volume through which the distal end has not been moved with a second color, and
 updating the illustrating to display the first color in real time as the second instrument is moved within the first portion so as to paint the determined volume.

14. The method of claim 13, further comprising:
predetermining a volume to remove from the subject prior to gaining access to the disc space of the subject with the first instrument.

15. The method of claim 14, wherein displaying the determination with the display device includes displaying a representation of an amount of the predetermined volume removed from the subject.

16. The method of claim 13, wherein the second color is an image representation color and the first color is different from the image representation color.

17. The method of claim 13, wherein displaying the determination with the display device includes displaying a value of the volume of the first portion.

18. A system for performing a procedure, comprising:
a first instrument operable to remove tissue from a subject;
a second instrument, having a distal end operable to contact a surface of a void formed during removal of the tissue with the first instrument;
a first tracking device connected to the second instrument;
a navigation system operable to:
 track the second instrument within the void; and
 determine a volume of the void based on the tracking the second instrument while moving the distal end of the second instrument within the void;
a display device operable to;
 display an image representative of the subject;
 display a first color with the display device to illustrate a first portion of the distal end; and
 update the illustrating to display and paint the first color in real time during the moving the distal end of the second instrument within the void formed in the subject to illustrate the volume of the void the distal end has traversed.

19. The system of claim 18, wherein the navigation system includes a memory having stored thereon a predetermined volume to remove from the subject prior to gaining access to the subject with the first instrument.

20. The system of claim 19, wherein the predetermined volume includes a volume of a spinal disc to remove during a discectomy.

21. The system of claim 18, wherein the first instrument is a non-tracked instrument that includes a cutting portion.

22. The system of claim 21, wherein the distal end of the second instrument has a known volume;
wherein the known volume is recalled by the navigation system to determine a volume through which the distal end has moved within the void and by contacting at least a wall defining the void.

23. The system of claim 22, wherein the distal end includes a trackable surface of the distal end;
wherein tracking the second instrument within the void includes determining a plurality of positions of the trackable surface and determining a volume based thereon.

24. The system of claim 23, wherein the navigation system further includes:
a processor system to execute instructions to determine a volume through which the distal end has passed.

* * * * *

UNITED STATES PATENT AND TRADEMARK OFFICE
CERTIFICATE OF CORRECTION

PATENT NO. : 10,828,113 B2
APPLICATION NO. : 15/997246
DATED : November 10, 2020
INVENTOR(S) : Anthony J. Melkent Page 1 of 1

It is certified that error appears in the above-identified patent and that said Letters Patent is hereby corrected as shown below:

In the Claims

Column 13, Line 23, Claim 13:
Delete "move" and insert --moved-- therefor; and

Column 14, Line 1, Claim 18:
Delete "instrument," and insert --instrument-- therefor; and Column 14, Line 10, Claim 18:
Delete "to;" and insert --to:-- therefor.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*